United States Patent [19]

Dickson et al.

[11] Patent Number: 5,047,340
[45] Date of Patent: Sep. 10, 1991

[54] LAC+ SACCHAROMYCES CEREVISIAE

[75] Inventors: Robert C. Dickson, Lexington, Ky.; Kotikanyadanam K. Sreekrishna, Bartlesville, Okla.

[73] Assignee: The University of Kentucky Research Foundation, Lexington, Ky.

[21] Appl. No.: 260,124

[22] Filed: Oct. 18, 1988

Related U.S. Application Data

[63] Continuation of Ser. No. 741,213, Jun. 5, 1985, abandoned.

[51] Int. Cl.$^5$ ...................... C12P 21/00; C12P 21/02; C12N 5/00
[52] U.S. Cl. ................................ 435/161; 430/172.3; 430/255; 430/256; 430/320.1; 430/172.1; 536/27; 935/37; 935/60; 935/69
[58] Field of Search .............. 435/68, 255, 256, 172.1, 435/172.3, 161, 320; 935/37, 60, 69; 536/27

[56] References Cited

U.S. PATENT DOCUMENTS 4,327,179 4/1982 Moebus et al. ................. 435/255 X
4,387,162 6/1983 Angle et al. .................... 435/256 X
4,418,150 11/1983 Gunge .

FOREIGN PATENT DOCUMENTS 8304050 11/1983 PCT Int'l Appl. .

OTHER PUBLICATIONS

Pandan et al., *J. Biol. Chem.* 258(9): 5666–5673 1983.
Buchel et al., *Nature* 283: 541–545 1980.
Pan thier et al., *Curr Genet* 2(2): 109–113 1980.
Sreekrishna et al., *Fed Proc.* 44(5): #6026 1985.
Sreekrishna et al., *Proc Natl. Acad Sci. U.S.A.* 82:7909–13 1985.
Marwaha et al., *Chem. Abstr.* 100: 101587k 1984.
Vanauvat et al., *Chem. Abstr.* 82: 137716a 1975.
Taya, M et al., Agric Biol. Chem. 48(9):2239–2243 1984.
Dickson, R. C. Gene 10: 347–356 1980.
Sherman et al., *Methods in Yeast Genetics* 1982 Cold Spring Harbor Publication pp. 112–120 "Cloning of Yeast Genes by Complementator".
Barr et al., *Fed. Proc.* vol. 39 (6) 1980 Abstract 1209 "Mutants of the Yeast" *Kluyseromyces–Luctis* defective or Lactose Uptake.
Dickson et al., *J. Bact* vol. 157(3) Jun. 1983 pp. 1245–1251 "Characterization of Lactose Transport in Kluyuveromyer Lactis".
Hinen et al., Proc. Natl. Acad. Sci. U.S.A., vol. 75, No. 4, pp. 1929–1933, Apr. 1978.
Terrell et al., Applied and Environmental Microbiology, Sep. 1984, pp. 577–580 (1984).
Webster et al., Gene, 26 (1983) 243–252.
Sreekrishna et al., Gene, 28 (1984) 73–81.
Dickson et al., Cell, vol. 15, 123–130, Sep. 1978.
Henikoff et al., Nature 289:33 (1982).
Paszewski et al., Acta Biochemica Polonica 17(4): 385 (1970).
Reeve, E.C.R. et al., Genetic Research 22:217 (1973).
Boy-Marcotte et al., Gene 20: 433 (1982).
Valenzuela et al., Science 228: 179 (1985).
DeFeo-Jones et al., Science 228: 179 (1985).

*Primary Examiner*—Robin L. Teskin
*Attorney, Agent, or Firm*—Lowe, Price, Leblanc, Becker & Shur

[57] ABSTRACT

The invention relates to novel, transformed strains of Lac+ *Saccharomyces cerevisiae*, capable of utilizing lactose as a sole carbon source, produced by inserting into the *Saccharomyces cerevisiae* a plasmid containing a lactose permease and a beta-galactosidase gene derived from *Kluyveromyces lactis* yeast.

18 Claims, 4 Drawing Sheets

FIGURE I

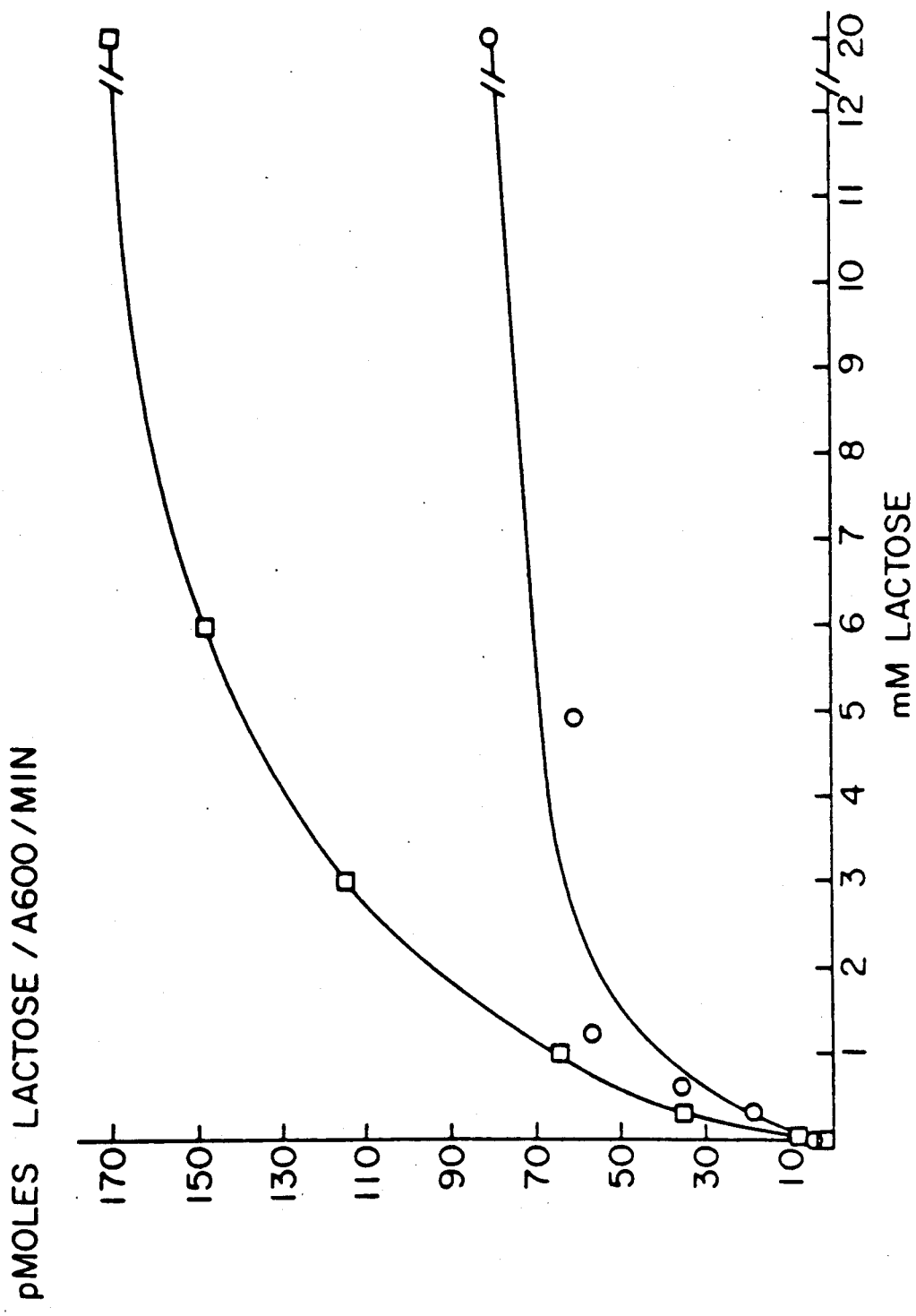

LAC+ SACCHAROMYCES CEREVISIAE

This application is a continuation of Application Ser. No. 741,213, filed June 5, 1985 now abandoned.

TECHNICAL FIELD

The invention relates to strains of the yeast *Saccharomyces cerevisiae* that have been transformed by insertion into the yeast of a plasmid containing the LAC4-LAC12 region from *Kluyveromyces lactis*, such that the *S. cerevisiae* acquires the ability to utilize lactose as a sole carbon source. The invention further relates to methods of selecting the transformed *S. Cerevisiae* strains.

BACKGROUND OF THE INVENTION

Whey, which is a byproduct of many commercial dairy processes, contains a large amount of lactose. The lactose in whey represents a large potential carbon and energy source, particularly for the production of ethanol. However, only a few commercial processes currently exist which utilize the lactose contained in whey, and converts it to a commercially useful product. Further, the existing processes are expensive, and, as a result, a great deal of whey is now disposed of, requiring costly waste treatment processes.

Various attempts to utilize the lactose contained in whey have included fermentation by strains of *Kluyveromyces fragilis* and other yeasts, especially *Saccharomyces cerevisiae*. The main problem with the use of *S. cerevisiae* is that it cannot ferment or utilize lactose directly. The lactose must first be hydrolyzed to form glucose and galactose, which the *S. cerevisiae* may then use. This procedure is inefficient since it produces high concentrations of extracellular glucose which cause catabolite repression of galactose utilization. Catabolite repression has been somewhat overcome by the selection of mutant strains that are resistant to repression. Despite these problems, *S. cerevisiae* is a desirable yeast to use in lactose utilizing processes since it has been used in the brewing and baking industries for many years, and procedures for its use on a commercial scale are highly developed. Further, *S. cerevisiae* may be genetically manipulated by various techniques, including genetic engineering. Finally, from the standpoint of basic research, it would be very advantageous to produce strains of *S. cerevisiae* that could grow on lactose because they could be used in a variety of mutant selection schemes, as has been accomplished with *E. coli*. It would therefore be advantageous to produce a strain of *S. cerevisiae* capable of direct lactose utilization and fermentation.

*S. cerevisiae* cannot use lactose because it lacks a betagalactosidase structural gene and therefore cannot hydrolyze lactose to glucose and galactose. Further, it has no mechanism for transporting lactose across its cell membrane. This lack of a lactose transport mechanism has been demonstrated by direct measurement of lactose transport in *S. cerevisiae* and by a showing that genetically engineered strains of *S. cerevisiae* that produce an intercellular betagalactosidase also do not grow on lactose. One method of creating a transport mechanism in *S. cerevisiae* would be to introduce a lactose permease gene, such as the lac Y gene of *E. coli*, into a strain of *S. cerevisiae* that has been genetically engineered to produce beta-galactosidase. However, this approach, for unknown reasons, has never proven successful. An alternative approach would be to incorporate into the *S. cerevisiae*, a lactose permease gene from another yeast.

The yeast *Kluyveromyces lactis* can grow on lactose as a sole carbon source, and is known to have an inducible lactose permease system. The genes coding for the permease have not yet been identified. Unsuccessful attempts have been made to isolate the lactose permease gene by transforming a *K. lactis* clone bank into a strain of *S. cerevisiae* that synthesizes beta-galactosidase and selecting transformants for growth on lactose.

SUMMARY OF THE INVENTION

One object of the present invention is to provide a genetically engineered strain of *Saccharomyces cerevisiae* which has the ability to utilize lactose as a sole carbon source.

Another object of the present invention is to transform a strain of *Saccharomyces cerevisiae* by inserting into the strain a plasmid containing the LAC4-LAC12 genes derived from *Kluyveromyces lactis*.

A further object of the present invention is to provide a method of transforming said *Saccharomyces cerevisiae* by inserting into said *S. cerevisiae* a plasmid containing the LAC4-LAC12 region of *K. lactis*.

A still further object of the present invention is to provide a plasmid containing the LAC4-LAC12 region derived from *K. lactis*.

An even further object of the present invention is to provide a strain of *S. cerevisiae* which can ferment lactose directly from whey, without a preliminary hydrolysis step wherein the lactose is first converted to glucose and galactose, and thus to provide an economical method of producing ethanol from whey.

A still further object of the present invention is to provide a method of constructing strains of *S. cerevisiae* and other yeast that grow on whey as a result of their ability to utilize lactose.

Other objects and advantages of the invention will become apparent as the description thereof proceeds.

In satisfaction of the foregoing objects and advantages, the present invention provides a genetically engineered strain of *Saccharomyces cerevisiae* that has the ability to utilize lactose as its sole carbon source. The *S. cerevisiae* is transformed by inserting into the *S. cerevisiae* a plasmid containing the lactose permease gene (LAC12) derived from *Kluyveromyces lactis*. The *S. cerevisiae* must also be transformed to contain a betagalactosidase structural gene each as the *K. lactis* gene LAC4 or the *E. coli* gene or by another method. The invention also provides the LAC4 and LAC12 containing plasmid, as well as methods for transforming and selecting the *S. cerevisiae* using said

BRIEF DESCRIPTION OF THE DRAWINGS

FIG. 4 demonstrates that lactose transport in Lac− *S. cerevisiae* is carrier-mediated.

DETAILED DESCRIPTION OF THE INVENTION

Figure 1:
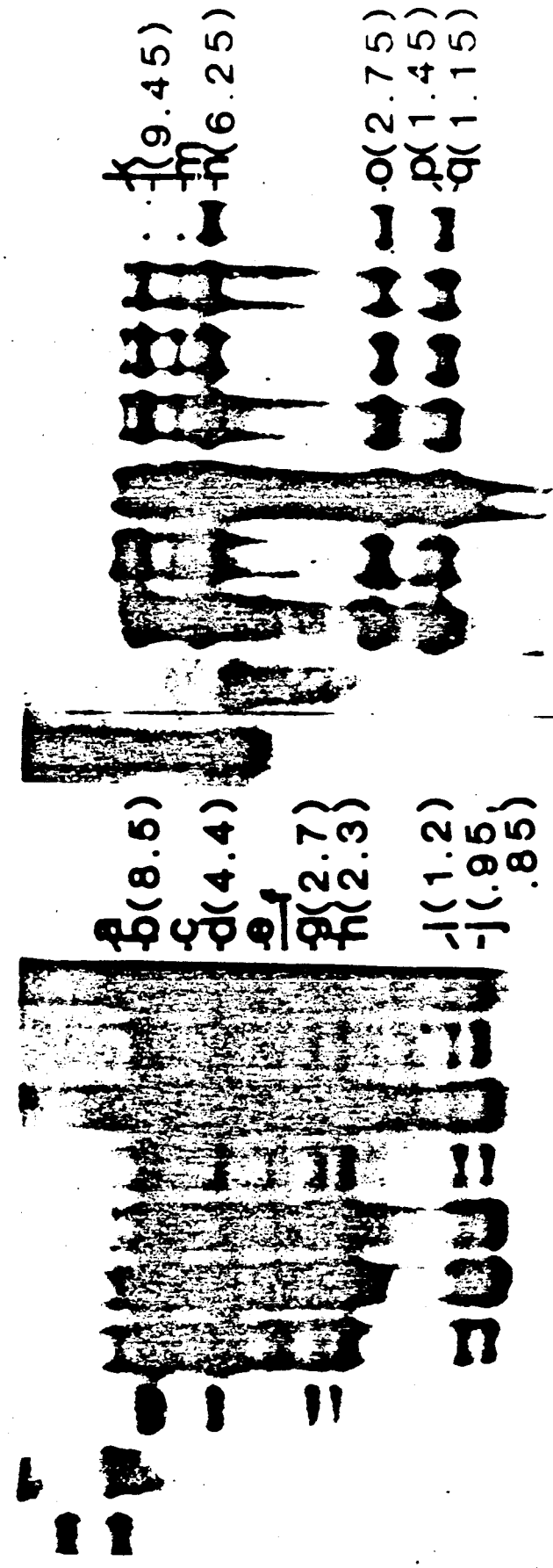
FIG. 1 represents Southern hybridization analysis of pKR1B-LAC4-1 sequences in Lac+ *S. cerevisiae*.

The invention relates to genetically engineered strains of *S. cerevisiae* which have been transformed so that they have the ability to utilize lactose as a sole carbon source. The *S. cerevisiae* is transformed by inserting into it a plasmid containing the LAC12 gene derived from *K. lactis*. In order to utilize lactose, the *S. cerevisiae* must additionally contain the betagalactosidase structural gene of *K. lactis*, LAC4, which may be transformed into the *S. cerevisiae* concurrently with the LAC12 gene, or may be inserted into the strain by a different method. Alternately, the lacZ gene derived from *E. coli* may be used instead of LAC4 if lacZ is fused to a yeast promoter thereby allowing synthesis of beta-galactosidase in yeast.

The invention further relates to plasmids containing the LAC12 gene from *K. lactis*, as well as methods of transforming *S. cerevisiae* by inserting said plasmids into the *S. cerevisiae*.

Two different strains of *S. cerevisiae* were used in the present invention. Strain L1582 produces high levels of beta-galactosidase enzyme activity due to fusion of a portion of the *E. coli* lac operon genes ZYA to the HIS4 promoter. Since this strain already produces beta-galactosidase, it should theoretically grow on lactose if a functional lactose permease system were introduced into it. Even though the strain already contained the lacY gene, which encodes for an *E. coli* lactose permease, the permease is apparently not functional since the L1582 strain does not grow on lactose. In addition, another strain of *S. cerevisiae*, YNN27 was also used. This strain did not contain any part of the *E. coli* lac operon. This strain has been shown to perform well in recombinant DNA experiments.

The plasmid of the present invention, pKR1B-LAC4-1 also contains the gene for resistance to the antibiotic G418 and a *K. lactis* ARS which allows replication in *K. lactis* and *S. cerevisiae*. The plasmid has a 14 kilobase (kb) fragment of *K. lactis* DNA containing the beta-galactosidase gene, LAC4, and, as shown below, an adjacent region of DNA that codes for a lactose permease, LAC12. In addition, the parent vector pKR1B was also used, which contains the G418 resistance gene, but does not contain the LAC4 or LAC12 genes.

The present invention provides strains of *S. cerevisiae* capable of utilizing lactose as a sole carbon source. The preferred species of this invention is *Saccharomyces cerevisiae* strain L1582 transformed with pKR1B-LAC4-1 and YNN27 transformed with pKR1B-LAC4-1. A culture of the transformed L1582, transformed YNN27, ATCC 20758, and of pKR1B-LAC4-1, ATCC 40186, have been placed on deposit with the American Type Culture Collection, 12301 Park Lawn Drive, Rockville, Md. 20852, and the accession numbers set forth have been assigned thereto. In each case, the deposit is restricted until such time as a patent has been issued disclosing the above deposits, except that access is available under 37 CFR 1.14 and 35 USC 122. After issuance of the patent, all restrictions on availability of the deposited cultures to the public will be irrevocably removed. The deposits will be maintained for a period of 30 years from the deposit date, and accordingly, the cultures will be permanently available to the public after issuance of the patent.

To construct the *S. cerevisiae* that grows on lactose, strain L1582 was transformed with pKR1B-LAC4-1 and cells were selected for resistance to G418. G418 resistant transformants were colony purified on YEPD/G418 plates and purified colonies chosen at random were spotted on MinLac plates (Minimal Lactose Medium) and YEPD plates, in that order. All colonies grew on the G418 and YEPD plates. Only 19% of the colonies grew on the MinLac plates. In another experiment, $10^2$ to $10^3$ G418 resistant transformed cells were spread on MinLac plates. Again, 19% of the G418 resistant colonies grew on lactose. As a control, L1582 was also transformed with the parent vector pKR1B. The G418 resistant transformants produced therefrom were selected and plated at densities of $10^6$ to $10^7$ cells on MinLac plates. No Lac+ transformants were ever observed.

To rule out the possibility that Lac+ cells were being produced as a result of some peculiarity of strain L1582, strain YNN27 of *S. cerevisiae* was also transformed. Again, the G418 resistant transformants were selected. Resistant colonies were pooled and plated on MinLac plates. Only about one cell in 250 G418 resistant cells produced a Lac+ colony, a frequency on the order of 1/50 that of strain L1582. Lac+ colonies were also never observed when YNN27 was transformed with parent vector pKR1B.

As additional evidence that pKR1B-LAC4-1 was responsible for the observed Lac+ phenotype, the simultaneous loss of the Lac+ and G418 resistance characteristics was determined. The G418 resistance phenotype was used to measure the presence or absence of the plasmid. This determination was based on the observation that vectors having ARS replicons are unstable and are lost from cells, particularly when no selective pressure is present. Lac+ L1582 were grown in YEPD medium without G418 selection for 10 generations. The frequency of G418 resistant cells decreased from about 20% initially to about 3%, indicating loss of the plasmid, and all G418 sensitive cells tested at the end of the growth period were Lac−. These results indicate that the Lac+ phenotype was mediated by the plasmid.

By contrast, when Lac+ YNN27 were grown in YEPD medium for 10 to 20 generations, more than 99% of the cells retained the G418 resistance marker, but only 10 to 30% were still Lac+. The stability of the G418 resistance phenotype suggested that the vector was integrating into a host chromosome.

Direct physical proof that Lac+ *S. cerevisiae* carried the pKR1B-LAC4-1, and that the plasmid had integrated into a host chromosome was obtained by Southern hybridization analysis using $^{32}$P-pKR1B-LAC4-1 as a hybridization probe. The Southern hybridization data are shown in FIG. 1. Total DNA was extracted from yeast and electrophoresed on 0.9% agarose gels and hybridized to $^{32}$P-pKR1B-LAC4-1. The numbers in parentheses in FIG. 1 represent kilobase pairs which were determined by comparison with lambda DNA molecular weight strands. Lanes A and K are purified pKR1B-LAC4-1, lane B is uncleaned L1582/pKR1B-LAC4-1, lane C corresponds to purified pKR1B-LAC4-1 cleaved with EcoRI, lanes D-J are L1582/pKR1B-LAC4-1 cleaved with EcoRI, lane L is uncleaned YNN27/pKR1B-LAC4-1, lane M is purified pKR1B-LAC4-1 cleaved with BamHI and BglII, and lanes N-S correspond to YNN27/pKR1B-LAC4-1 cleaved with BamHI and BglII.

As set forth above, total uncleaved DNA isolated from 7 independent Lac+ L1582 transformants showed a band of hybridization corresponding to chromosomal DNA (for example, FIG. 1, lane B). If the vector had been present in the unintegrated or autonomous state, two bands would have hybridized, the faster migrating band being supercoiled, and the other being open-circular DNA (lane A). A lack of these two bands of hybridization thus confirmed plasmid integration. Further evidence of plasmid integration was obtained using total DNA cleaved with the EcoRI restriction endonuclease. If one copy of the plasmid integrated, one of six EcoRI vector fragments should have been absent (while 8 fragments were present, the smallest runs off the gel and two of the fragments comigrate as band j), and there should have been two new bands representing chromosomal sequences flanking the integrated vector. The size of the two chromosomal sequences could not be predicted. If more than one copy of the vector had integrated tandemly, as often happens, all six of the vector bands plus two new bands would have been observed. All seven DNA samples (lanes D-J) gave the same pattern containing six vector bands (bands b, d, g, h, i and j) plus four unique but faint bands (bands a, c, e and f). Because four rather than two new bands were present, it is likely that the plasmid had integrated at two chromosomal locations. Based on densitometer scans of autoradiograms, and assuming one copy of each unique sequence per transformed cell, three to five copies of the plasmid would be present per cell. It cannot be determined from the above data whether some cells had plasmid integrated at one or both sites, and whether one site had only one copy of the plasmid while the other site had multiple tandem copies.

Southern hybridization experiments showed that pKR1B-LAC4-1 had integrated into a chromosome of YNN27 since total DNA from 6 Lac+ transformants gave one band of hybridization corresponding to chromosomal DNA. A representative of the six samples is shown in lane L. To determine if integration had occurred at a single site, and if multiple copies had integrated, the Southern hybridization experiment was repeated using total DNA cleaved with the restriction endonucleases BamHI and BglII. All DNA samples (lane N-S) contained 5 bands (lanes l,n,o,p,q) corresponding to plasmid fragments plus two less intense bands (k and m). Thus, the Lac +YNN27 contained multiple tandem copies of pKR1B-LAC4-1 and, by contrast to Lac+ L1582, integration had occurred alone chromosomal site. Based on densitometry scans of autoradiograms, three to five copies of the plasmid were present per cell. In control experiments, $^{32}$P-pKR1B-LAC4-1 did not hybridize to DNA from untransformed L1582 or YNN27.

In addition, further evidence indicated that pKR1B-LAC4-1 conferred the Lac+ phenotype on its host. Usually total DNA from transformed yeasts that integrate the vector cannot transform E. coli because there are not autonomous copies of the vector. However, some Lac+ transformants of both L1582 and YNN27 gave total DNA preparations which would transform E. coli for ampicillin and kanamycin resistance. Plasmid DNA prepared from such E. coli had the same EcoRI and BamHI/BglII restriction fragment patterns as authentic pKR1B-LAC4-1. Further, this plasmid DNA conferred the G418 resistance and Lac+ phenotypes on either L1582 or YNN27 to the same degree as the original pKR1B-LAC4 DNA preparation.

Figure 2:
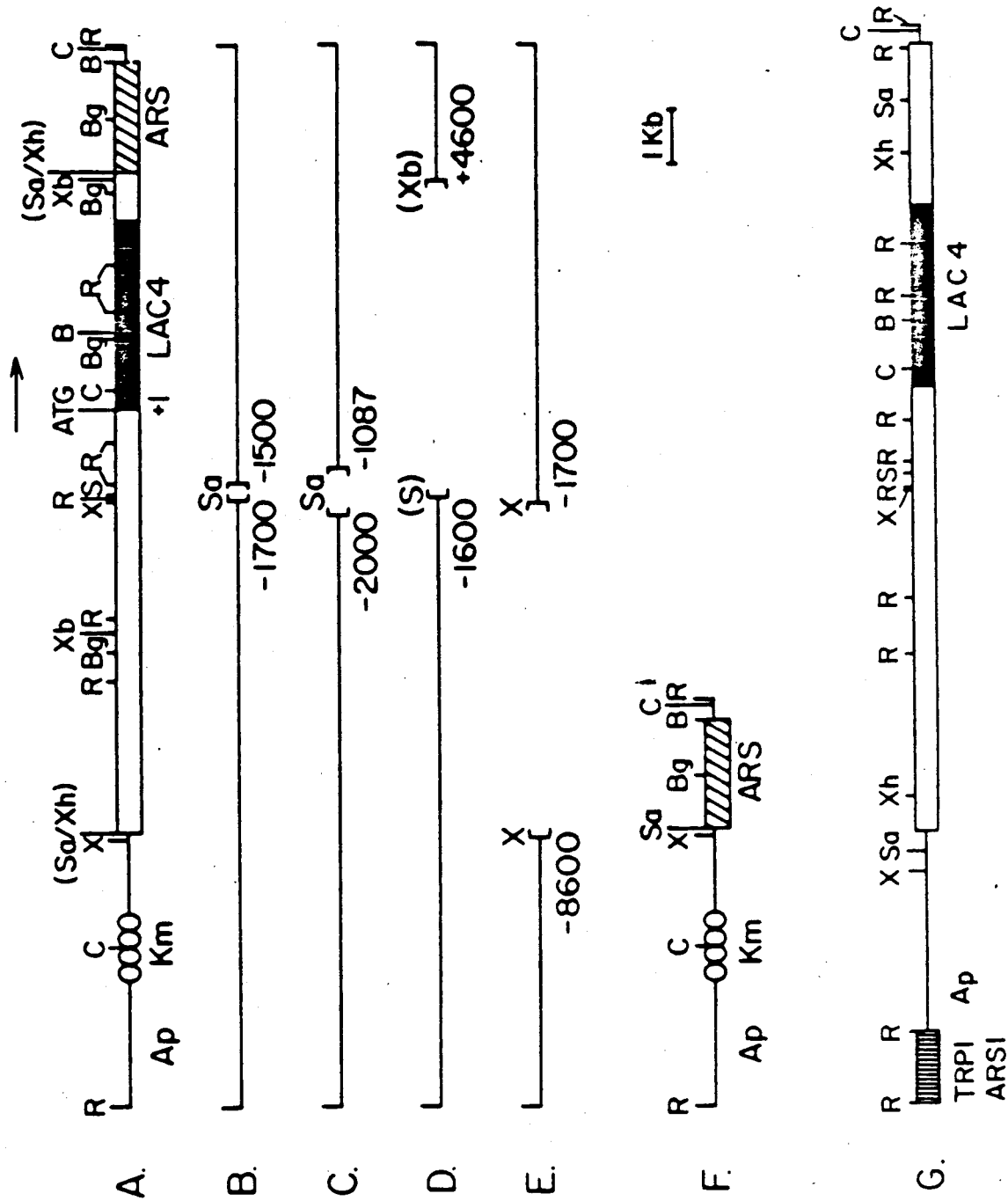
FIG. 2 sets forth the structure of the yeast plasmids described in the present invention. Plasmid A represents the pKR1B-LAC4-1, and the other plasmids B, C, D and E are derivatives of plasmid A, carrying specific deletions therefrom. Plasmid G is pBN53 from which the *K. lactis* region of pKR1B-LAC4-1 was obtained.

In order to determine which region of pKR1B-LAC4-1 was responsible for the Lac+ phenotype, L1582 was transformed with a set of deletion plasmids as shown in FIG. 2. FIG. 2 shows the construction of the pKR1B-LAC4-1 plasmids and the specific deletions thereof. The structure of the basic pKR1B has been described in Bhairi, S. M., 1984, Ph.D. thesis, University of Kentucky, Lexington, Ky., hereby incorporated by reference. The plasmid carries bacterial genes conferring resistance to ampicillin (Ap) and kanamycin (Km) from Tn903, plus the pBR$^{322}$ origin of DNA replication that allows replication in E. coli, and a K. lactis autonomous replication sequence (ARS) that allows replication in both K. lactis and S. cerevisiae. In yeast, the Km gene confers resistance to the antibiotic G418. In plasmid A, the direction of transcription of LAC4 is shown by an arrow above the diagram, and its ATG initiation codon is indicated. DNA sequences are diagrammed as follows. The solid thin line indicates E. coli plasmid pBR$^{322}$, the circles represent Tn903 sequences, the open bars stand for K. lactis sequences, the solid bar represents LAC4 of K. lactis, the diagonal hatched bars indicate K. lactis ARS1B. The vertical cross-hatched bars represent the TRP 1 and ARS1 regions of S. cerevisiae. The restriction endonuclease sites are as follows: R represents EcoRI, B stands for BamHI, C indicates ClaI, Sa represents SalI, Xh depicts XhoI, Xb refers to XbaI, Bg indicates BglII, S represents SstII, X identifies XmaIII. The restriction sites shown in parentheses were inactivated during plasmid construction. Plasmids D-E represent deletions of plasmid A as follows: B represents Δ1500, C indicates Δ1087, D indicates ΔS-X, and E represents ΔX. Plasmid G is pBN53.

After transformation of the L1582 strain with the set of deletion plasmids as set forth in FIG. 2, the G418 transformants obtained were plated on MinLac plates at 10$^4$ and 10$^6$ cells/plate. Lac+ colonies were obtained with plasmids B, C, and D, but none were obtained with E. Therefore, it is concluded that the region of pKR1B-LAC4-1 between −2000 and −8600conveys the Lac+ phenotype on strain L1582. The region of pKR1B-LAC4-1 between −2000 and −8600 is believed to code for a lactose permease. Because YNN27 lacks a beta-galactosidase gene, it can only be transformed to the Lac+ phenotype by plasmids having a betagalactosidase structural gene LAC4 in addition to an intact −2000 to −8000 region, plasmids A, B and C.

Figure 3:
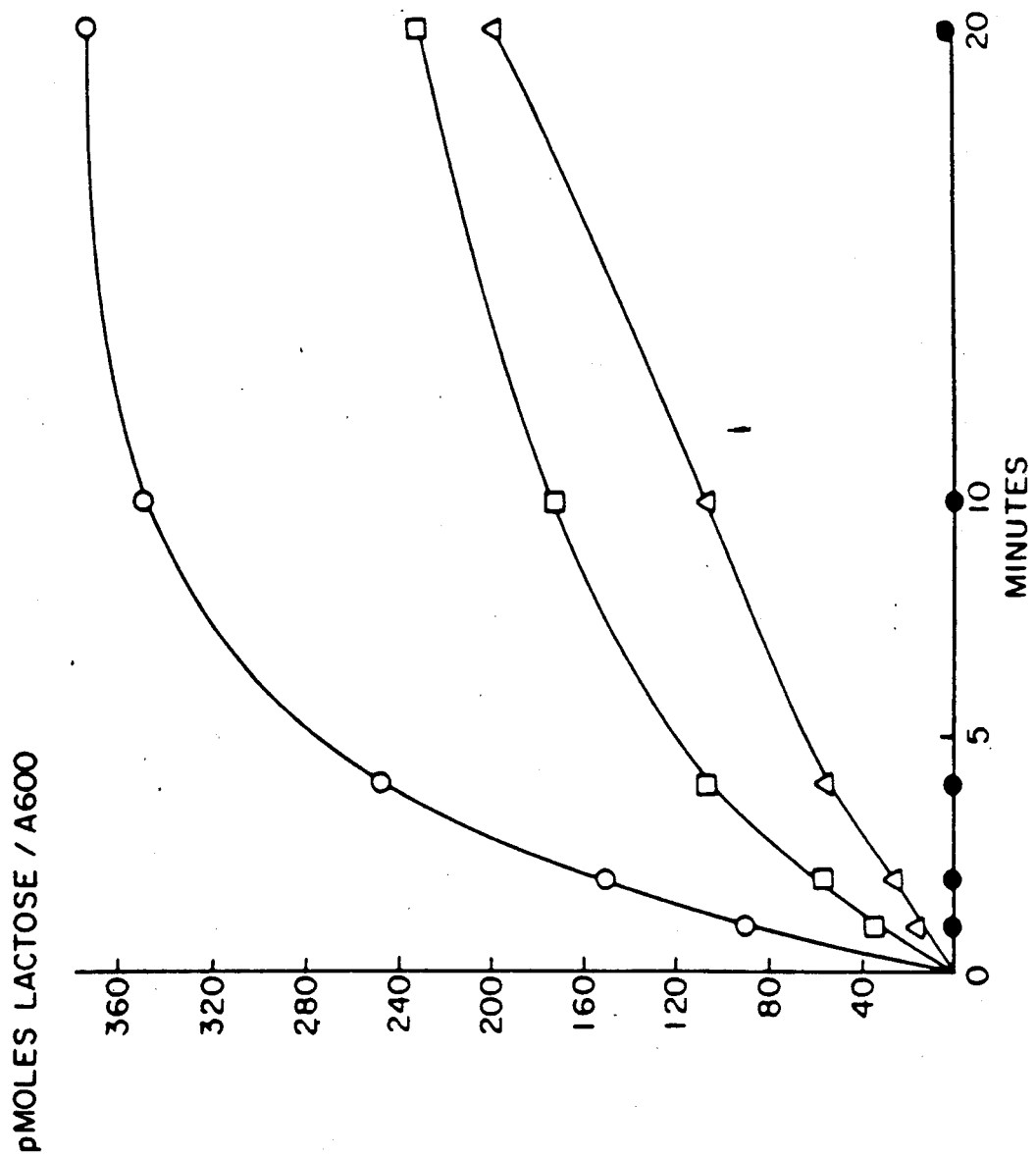
FIG. 3 sets forth the kinetics of lactose transport in Lac+ *S. cerevisiae*.

If pKR1B-LAC4-1 confers the Lac+ phenotype on S. cerevisiae because it codes for a lactose permease, then the lactose transport in Lac+ S. cerevisiae and K. lactis should have similar properties. The kinetics of lactose transport were first measured to determine if Lac+ S. cerevisiae transported measurable quantities of lactose and to determine the time scale over which the apparent initial velocity of transport could be measured. The results are set forth in FIG. 3. For the purposes of FIG. 3, the final concentration of lactose was 0.5 mM. The samples in FIG. 3 are as follows. ○—○ represents K. lactis strain MS425/pKR1B, □—□ represents S. cerevisiae strain L1582/pKR1B-LAC4-Δ1087, △—△ represents S. cerevisiae strain YNN27/pKR1B-LAC4-1, and ●—● represents S. cerevisiae strain L1582/pKR1B. Both Lac+ S. cerevisiae strains L1582/pKR1B-LAC4-Δ1087 and YNN27/ pKR1B-LAC 4- 1 transported easily measured pmole amounts of lactose, although at a slower rate than K. lactis strain MS425/pKR1B. The lactose transport was linear up to at least three minutes, thus allowing measurement of apparent initial velocity. FIG. 3 indicates that a control strain of S. cerevisiae L1582 transformed with the parent vector pKR1B did not transport lactose.

Lactose transport mediated by a membrane-bound permease is demonstrated by saturation of the transport process at high concentrations of lactose. Alternatively, transport by simple diffusion across the membrane is demonstrated by a lack of saturation. FIG. 4 indicates that lactose transport in Lac+ S. cerevisiae is carrier mediated. The rate of lactose transport as a function of substrate concentration is shown for two experiments using Lac+ L1582/pKR1B-LAC4-1 (o—o) and Lac+ L1582/pKR1B-LAC4-Δ1087 (□—□). For each concentration of lactose, the rate of transport represented the average of samples taken at 30, 60, and 90 seconds. Thus, FIG. 4 shows that lactose transport in Lac+ cells becomes saturated with increasing concentrations of lactose. The data disclosed in FIG. 4 gave apparent Km values of 0.97 and 1.09 mM for lactose transport. K. lactis strain MS425 gave an apparent Km of 0.67+0.11 for lactose transport.

Carrier-mediated membrane transport processes display a high degree of stereospecificity for substrate. Thus, the L1582/pKR1B-LAC4-1 will show the same stereospecificity for substrate as K. lactis if pKR1B-LAC4-1 carries a K. lactis gene coding for a lactose permease. Stereospecificity is shown by measuring how well a compound inhabits lactose transport (See Table 1). Lactose is a 4-0-beta-D-galactosyl-D-glucose, a beta-galactoside, and thus lactose transport is inhibited only weakly by alphagalactosides, melibiose, and 4-nitrophenyl-alpha-D-galactose. The lactose permease shows specificity for a disaccharide because the monosaccharide galactose gave only moderate inhibition. The permease also preferred an O-linkage to a thio-linkage since thiogalactoside gave only moderate inhibition. The strongest inhibition was shown by a disaccharide with a beta-O-linkage, 3-O-beta-D-galactosyl-D-arabinose.

TABLE I

Sterospecificity of Lactose Transport

| Competing Compound | % Inhibition of Lactose Transport[a] | |
|---|---|---|
| | K. lactis MS425/ pKR1B | S. cerevisiae L1582/ pKR1B-LAC4-1 |
| None | 0 | 0 |
| D-galactose | 26 | 24.3 ± 7.2 |
| 6-0-α-D-galactosyl-D-glucose (melibiose) | 10 | 10.7 ± 8 |
| 3-0-β-D-galactosyl-D-arabinose | 93 | 90 ± 6 |
| 4-nitrophenyl-α-D-galactoside | 6 | 1.1 ± 1 |
| D-galactosyl-1-thio-β-D-galactoside (thiodigalactoside) | 28 | 4.9 ± 4 |

[a]Cells were prepared for lactose transport measurements as described in Example 8.

After warming the cells to 23° C. the competing compound was added to a final concentration of 50 mM. Thirty seconds later [$^{14}$C] lactose was added to a final concentration of 1 mM and 100 μl samples were filtered 1 and 2 minutes later. The concentration of inhibitor was chosen so that if it had the same $K_m$ for transport as lactose (1 mM used for the calculation), lactose transport would be inhibited by 97% (50 Km/50 Km+Km+0.25 Km=% inhibition). For K. lactis the experiment was done twice and for S. cerevisiae it was done three times. Averaged values with or without a standard deviation are shown.

Finally, the lactose transport in LAC+ S. cerevisiae was determined to be an energy-dependent process, as it is in K. lactis. To measure energy dependence, cells were pre-incubated for 20 minutes with 1 mM 2,4-dinitrophenol at ambient temperature. Lactose transport was inhibited almost completely both in the Lac+ strain of S. cerevisiae, L1582/pKR1B-LAC4-1, and in the K. lactis strain MS425/pKR1B.

The growth rate of Lac+ S. cerevisiae was determined by measuring the doubling time of cells. Strains were pre-grown to logarithmic phase in MinLac medium, then diluted to fresh medium, and the absorbance was measured. Doubling times were as fllows: K. lactis wild type strain Y1140 was 1.6 hours, S. cerevisiae strain L1582/pKR1B-LAC4-1 was 13.0 hours, L1582/pKR1B-LAC4-Δ1087 was 10.0 hours, and YNN27/pKR1B-LAC4-1 was 6.7 hours. These growth rates were reflected in the growth rate of colonies on MinLac plates.

Additional evidence that the −2000 to −8600 region of pKR1B-LAC4-1 codes for a K. lactis lactose permease was obtained by demonstrating that a mutation mapping 1.6 centiMorgans from LAC4 produces a permease minus phenotype. This mutation and the permease minus phenotype can be complemented by pKR1B-LAC4-1 or plasmids, B, C or D, shown in FIG. 2. A mutant strain of K. lactis defective in lactose transport was obtained by plating $10^5$ to $10^7$ cells of strain 13C476 on MinLac plates containing dextrose plus 40μg of 5-bromo-4-chloro-3-indolyl-β-D-galactoside (Xgal) per ml. Strain 13C476 will not grow on this medium because the lactose is hydrolysed to galactose which inhibits growth due to a mutation in the galactosyl epimerase (EC 5.1.3.2) structural gene, gal10. Revertants that become resistant to lactose and thus allow growth on these plating conditions can arise by mutation in one or more genes including reversion of the original gal10-1 mutation in stra in 13C476, mutation in the galactokinase structural gene, GAL1, mutation in a positive regulatory gene, and mutation in the lactose permease gene. After several days of incubation lactose-resistant revertant colonies appeared at a frequency of one in $10^6$ cells. These were picked, colony purified, and backcrossed to a Lac+ strain of K. lactis. In this manner the mutation that gave rise to the lactose-resistant phenotype could be separated from the original gal10-1 and lacl0c mutations carried by K. lactis strain 13C476. Lactose-resistant mutants that showed a white or light blue colony color on MinLac plates containing dextrose and Xgal were selected for further study. A defect in the lactose permease should produce a cell that would not grow on lactose and would not showinduction of beta-galactosidase and the galactose catabolic enzymes. This lack of induction, which is due to exclusion of the inducer lactose, would yield white colonies on the Xgal indicator plates. Lactose-inducible enzymes were measured on cell-free extracts prepared from cells grown on double strength yeast nitrogen base (Difco) containing 2% sorbitol plus required nutrients either in the absence (uninduced) or presence of 2% galactose (induced). Under these conditions wildtype K. lactis strain Y1140 had uninduced beta-galactosidase and galactokinase specific activity levels of 100 and 5 units, respectively, and induced levels of 6500 and 100, respectively. A lactose-resistant mutant strain, called 11D304, showed uninduced beta-galactosidase and galactokinase levels of 190 and 10, respectively, and induced levels of 4000 and 90, respectively. Therefore this strain induced beta-galactosidase and galactokinase normally. In contrast, strain 11D304 when grown under the same inducing conditions as for the enzyme activity assays, failed to showinduction of transport activity. Lactose transport activity was measured as described in Example 10. Strains Y1140 and 11D305 had uninduced lactose transport activities of 40 and 1.3 picomoles of lactose/$A_{600}$/minute, respectively, and values of 800 and 4.5, respectively, after induction for 24 hours by growing in medium containing 2% galactose. The lactose transport data demonstrate that strain 11D304 has about 30-fold less basal transport activity than wild type strain Y1140 and the transport activity is only induced about 2 to 3-fold, which is much less than the 20-fold induction seen in strain Y1140. Thus, strain 11D305 carries a mutation in the lactose permease structural gene, designated LAC12. The lac12-230 mutation in 11D304 was mapped with respect to LAC4 by tetrad analysis. Data are summarized below:

TABLE II

| cross | Type of Tetrad | | |
|---|---|---|---|
| | Parental Ditype (0 Lac+:4 Lac−) | Tetra Type (1 Lac+:3 Lac−) | Non-Parental Ditype (2 Lac+:2 Lac−) |
| Lac 12-230 × lac4-8 | 86 | 3 | 0 |
| Lac 12-230 × lac4-14 | 65 | 0 | 0 |
| Lac 12-230 × lac4-23 | 18 | 2 | 0 |
| Lac 12-230 × lac4-30 | 19 | 0 | 0 |
| | 188 | 5 | 0 |

These tetrad data show that LAC12 maps 1.6 centimorgans from LAC4.

A mutation which maps 1.6 centiMorgans from LAC4 could occur in the chromosomal region that is homologous to the −2000 to −8600 region of pKR1B-LAC4-1. If this were true then pKR1B-LAC4-1 or a derivative of it carrying the −2000 to −8600 region, plasmids B, C and D in FIG. 2, should complement the 12-230 mutation in strain 11D304 and convert the strain from a permease minus (Lac−) to a permease plus (Lac+) phenotype. This implies that the −2000 to −8600 region of pKR1B-LAC4-1 codes for a lactose permease. To test this hypothesis strain 11D305 was transformed with plasmids A,B,C,D,E and F (FIG. 2). Transformed cells were first selected for resistance to G418 and then screened for growth on MinLac plates by replica plating or streaking for single colonies. Plasmids A,B,C and D give rise to Lac+ colonies and therefore complemented the mutation 12-230. Plasmids E and F did not give rise to Lac+ colonies and therefore did not complement the mutation 12-230. Thus, the region of pKR1B-Lac4-1 between −2000 and −8600 codes for the K. lactis lactose permease.

Therefore, the present invention provides a microorganism which has the characteristics of a strain of S. cerevisiae which is capable of utilizing lactose as a sole carbon source. S. cerevisiae having this characteristic can thus utilize lactose directly, without a preliminary step of first hydrolyzing the lactose to form glucose and galactose, as is necessary with wild type S. cerevisiae. This characteristic provides an economical and efficient method of obtaining chemical products, such as ethanol, by conversion of the lactose in whey, a by-product of the cheese industry.

The following examples are presented to illustrate the invention, but it is not to be considered as limited thereto. In the examples and throughout the specification, parts are by weight unless otherwise indicated.

In the examples, the following materials were used:

E. coli : Strain DG75 (hsdl leu6 ara14 galK2 mtl1 rpsL20 thi1 supE44 lacΔZ39 λ) was used for all bacterial transformations and plasmid propagations.

S. cerevisiae: Strains YNN27 (αtrp1-289 ura3-52 gal2, Stinchomb et al (1980) Proc. Natl. Acad. Sci. U.S.A. 77, 4559–4563); L1582 (αino HIS4::lacZ) was obtained from G. R. Fink, Massachusetts Institute of Technology, Cambridge, Mass.

K. lactis : Wild type strain Y1140 (a lacI LAC2) and mutant strain MS425 (αlac4-8 adel-1) and strains with the alleles lac4-14, lac4-23 and lac4-30 have been described in Sheetz, R. M. and Dickson, R. C. (1981) Genetics 98, 729–745, hereby incorporated by reference.

Other mutant strains of K. lactis (unpublished results) include 13C476 (lac10$^c$-1 gall0-1 his2-2 met2-2 trp1-1) and 11D305 (lac12-230 his2-2).

The antibiotic G418 sulfate was obtained from Grand Island Biologicals (Grand Island, N.Y.), and the antibiotics kanamycin and ampicillin were from Sigma (St. Louis, Mo.). Restriction enzymes, enzyme grade bovine serum albumin and DNA polymerase I (Klenow fragment) were products of BRL (Bethesda, Md.). D-Glucose-[$^{14}$C]lactose was from Amersham (CFA 278; 58mCi/mM; Lexington, Mass.). Bromochloroindole galactoside (X gal) was purchased from Research Organic Inc., Cleveland, Ohio.

YEPD contained 20 g glucose, 20 g peptone and 10 g yeast extract per liter. Minimal lactose medium (MinLac) contained 3.4 g yeast nitrogen base (Difco, without amino acids or ammonium sulfate), 10 g ammonium sulfate, 20 g lactose, 10 mg uracil, 40 mg leucine, 40 mg tryptophan and 40 mg histidine per liter. Petri plates of the above media contained 15 g agar/liter.

Plasmid pKR1B has been described hereinabove (See FIG. 2). pKR1B has also been described in Sreekrishna, K., Webster, T. D. and Dickson, R. C. (1984) Gene 28:73–81. E. coli were transformed according to the method of Dagert, M. and Ehrlich, S. D. (1979) Gene 6:23–28. Small and large scale preparations of plasmid DNAs were obtained from E. coli by the method of Birnboim, H. C. and Doly, J. (1979) Nucl. Acids Res. 1513–1523. Purified supercoiled plasmid DNA was obtained by CsCl-EtBr density gradient centrifugation. Yeasts were transformed according to the procedure of Hinnen, A., Hicks, J. B. and Fink, G. R. (1978) Proc. Natl. Acad. Sci. U.S.A. 75:1929–1933 and transformants resistant to the antibiotic G418 were selected using the scheme of Webster, T. D. and Dickson, R. C. (1983) Gene 26:243–252. Total yeast DNA from both untransformed and transformed cells were prepared by the method of Struhl, K., Stinchcomb, D. T., Scherer, S. and Davis, R. W. (1979) Proc. Natl. Acad. Sci. U.S.A. 6:1035–1039. Southern hybridization has been described (Southern, E. M., 1975, J. Mol. Biol. 98:503–517). The other plasmids are described in Example 3 and were described in Bhairi, S. M., 1984, Ph.D. Thesis, University of Kentucky, Lexington, Ky.

EXAMPLE 1

*K. lactis* DNA was prepared as follows. *K. lactis* strain Y1140 was grown to stationary phase in double strength yeast nitrogen base (Difco) containing 1% glucose and was diluted into fresh medium to give an initial density of 0.3 $A_{600}$ units/ml. Growth at 30° C. was continued until density reached a value of 11 $A_{600}$ units/ml. Cells were harvested by centrifugation at 5000 X g for 5 minutes in a GS3 Sorvall rotor at room temperature. The cell pellet was resuspended in one-tenth volume of 1.2M sorbitol, 50 mM $NaPO_4$ (pH 7.9), 20 mM dithiothreitotl. Zymolyase 60,000 (Miles Laboratories) was added to a final concentration of 40 μg/ml and the culture was incubated at 30° C. with gentle shaking. Extent of conversion to spheroplasts was monitored by comparing the cell count following a tenfold dilution into 1.5M sorbitol with a ten-fold dilution into 5% sodium dodecyl sulfate. When greater than 80% of the cells were converted to spheroplasts, the sample was centrifuged for 5 minutes at 1000 X g at room temperature. The spheroplasts were suspended in 1/200 of their original volume using a 1.5M sorbitol solution. Three volumes of PLBII (0.1M NaCl, 0.02M EDTA, pH 7.0) and 1 volume of DM solution (10 mM Tris-HCl, 20 mM EDTA, 2% sarcosyl, 3% deoxycholate, 5% sodium dodecyl sulfate, pH 8.0) were added and the mixture was gently shaken on a rocker platform for 20 minutes. A mixture of 4 volumes of PLBII and 1 volume of DM was added to give a final A260 value of 10 units/ml and the solution was extracted with an equal volume of phenol:chloroform (1:1) saturated with PLBII. Extraction with phenol:chloroform was repeated for a total of three times, after which the aqueous phase was extracted once with an equal volume of chloroform. The aqueous phase was adjusted to 0.25M NaCl and the DNA was precipitated with 2 volumes of 95% ethanol at −20° C. overnight. DNA was centrifuged at 5000 X g for 20 minutes at 4° C. in a GAS Sorvall rotor. The DNA pellet was suspended in 15 to 20 mls of 50 mM Tris (pH 7.0) and CsCl was added to a final concentration of 0.95 gm/ml (Refractive Index:1.4000). DNA was banded by equilibrium centrifugation at 55,000 rpm for 20 hours in a Ti70 Beckman rotor at 20° C. Fractions were collected from the bottom of the tube by punching a hole with an 18 gauge needle. Every fourth fraction was analyzed for the presence of DNA by electrophoresis of a 30 μl sample on a 0.8% agarose gel. The fractions containing DNA were pooled and precipitated overnight with 3 volumes of 70% ethanol at 4o and reprecipitated with 0.3M sodium acetate and 3 volumes of 95% ethanol at −20° C. The DNA was dissolved in 10 mM Tris (pH 8.0), 1 mM EDTA.

EXAMPLE 2

*K. lactis* DNA fragments of 10-25 kb were isolated as follows. Initially a small scale digestion of *K. lactis* DNA of Example 2 was set up to determine the optimal concentration of the Sau3A enzyme and the DNA, and to determine the period of incubation required to achieve a maximum yield of 10-25 kb DNA fragments. For large scale digestion these parameters were increased proportionately. For example, five reaction tubes each containing 200 μg of *K. lactis* DNA in 1 ml of medium salt buffer (Bethesda Research Laboratories) plus 100 μg/ml BSA were equilibrated at 37° C. Six units of Sau3A restriction endonuclease (Bethesda Research Laboratories) were added to each tube and the tubes were incubated for 10, 15, 20, 30 and 35 minutes. The digestions were terminated by adding EDTA to a final concentration of 15 mM and heating at 65° for 10 minutes. To concentrate the DNA the contents of five tubes were pooled and extracted twice with phenol:chloroform(1:1) saturated with 50 mM Tris-HCl (pH 8.0), 1 mM EDTA. The aqueous layer was extracted with an equal volume of ether and the ether was removed by heating at 60° C. for 10 minutes. DNA was precipitated with 0.3M sodium acetate and 3 volumes of 95% ethanol overnight at −20° C. The sample was centrifuged at 12,000 X g for 30 minutes at 4° C. in an HB4 Sorvall rotor. The pellet was washed with 70% ethanol, dried, dissolved in 1 ml of 5 mM EDTA (pH 8.0) at a concentration of 1 mg/ml and loaded on a sucrose gradient prepared as follows. Sucrose solutions (40% (w/v) and 10% (w/v)) were made in 1M NaCl, 20 mM Tris (8.0), 5 mM EDTA and sterilized by autoclaving for 15 minutes. The gradient apparatus (Buchler Instruments, Fort Lee, N.J.) and the teflon tubing were thoroughly cleaned with distilled water, 0.1% diethyl pyrocarbonate, 5 mM EDTA, and sterile deionized water in that order. Sau3A digested DNA (250 μg in 250 μls) was layered on a gradient and the gradient was centrifuged at 26,000 rpm for 30 hours at 20° C. in a Beckman SW27 rotor. Thirty-drop fractions were collected from the bottom of the gradient by pumping with a peristaltic pump. Thirty microliters of every fifth fraction were electrophoresed on a 0.8% agrose gel to determine the presence of DNA and also to estimate its size. Fractions containing 10-25 kb DNA fragments were pooled and precipitated with an equal volume of isopropanol at −20° overnight. The sample was centrifuged in a Sorvall HB4 rotor at 12,000 X g for 30 minutes at 4° C. The DNA pellet was resuspended in water and reprecipitated with 0.3M sodium acetate (pH 4.8) and 2 volumes of ethanol. The DNA pellet was dissolved in 1 mM EDTA (pH 8.0).

EXAMPLE 3

The plasmid pKR1B-LAC4-1 was constructed as follows:

Three micrograms of YRp7 plasmid DNA (Struhl, K., et al 1979) were digested with 10 units of Bam Hl in 50 μl of buffer (Bethesda Research Laboratories, Bethesda, Md.) containing 100 μg/ml of BSA for 90 minutes at 37° C. The reaction mixture was diluted to 250 μl with 50 mM Tris (pH 8.0) 5 mM $MgCl_2$, and incubated with 2 units of calf intestine alkaline phosphatase at 37° C. for 15 minutes and then at 60° C. for 15 minutes. The reaction mixture was twice extracted with phenol: chloroform: isoamyl alcohol (25:24:1) saturated with 50 mM Tris (pH 8.0) and 1 mM EDTA to remove the enzyme. Phenol was removed by extracting with ether. Ether was removed by heating at 60° C. for 10 minutes. The DNA was precipitated with 0.3M sodium acetate and 67% ethanol, and dissolved in 60 μl of water.

Phosphatase-treated vector (0.5 μg) was mixed with 1 to 2.5 μg of 10-25 kb *K. lactis* Sau3A-generated DNA fragments (see Example 2) in 300 μl of T4 DNA ligase buffer supplemented with 100 μg/ml BSA and incubated with 2 units of T4 DNA ligase at 4° C. for 16 hours.

One-hundred microliters of competent *E. coli* DG75 were transformed by incubation with 30 μl portions of the ligated DNA at 0° C. for 25 minutes and heated at 37° C. for 3 minutes. The cells were allowed to grow at 37° C. for 1 hour in 1 ml of LB medium to allow expression of plasmid encoded genes. The transformation mixture from several tubes was pooled, centrifuged and suspended in 1 ml of LB medium. One-hundred microliters of cells were spread on LB-ampicillin plates and incubated at 30° C. for 20-24 hours. The transformants from several plates were pooled, centrifuged, and suspended in 5 ml of 50% glycerol, 5 mM MgCl$_2$. They were stored in 500 μl portions at −20° C. and will be referred to below as the Sau3A clone bank.

EXAMPLE 4

The Sau3A clone bank produced in Example 3, was screened for the presence of a plasmid carrying LAC4 by in situ colony hybridization using the $^{32}$P-labelled 2.4 kb EcoRI fragment of pK16 (Dickson, R. C. and Markin, J. S. 1978. Cell 15:12-130) as a hybridization probe. This EcoRI fragment contains the ATG codon of LAC4 as shown on plasmid A in FIG. 2. For this purpose the Sau3A clone bank was spread on ten LB-Ampicillin plates (5,000 cells per plate) conta in ing Xgal, the chromogenic substrate for beta-galactosidase. The substrate was included to screen for colonies that might fortuitously express LAC4 and could be recognized by their blue color. Several blue colonies (about 20 per plate) were observed after 16–20 hours of incubation at 30° C. Colonies from each plate were transferred to Whatman 541 filters, chloroamphenicol amplified and hybridized to the probe according to the procedures of Gergen, J. P., Stern, R. H. and Wensink, P. C. (19 79) Nucl. Acids Res. 7:2115–2136. Autoradiography revealed that all the blue colonies hybridized to the probe as expected. Blue colonies were colony-purified by repeated streaking on ampicillin plates containing Xgal and screened for tetracycline sensitivity. Of the 140 colonies tested, 20 turned out to be tetracycline sensitive as expected if a Sau3A fragment had been cloned into the BamHI site which is in the tetracycline gene of the vector. Small scale DNA was prepared from the 20 blue tetracycline-sensitive colonies.

The EcoRI restriction pattern of each of these DNAs was determined on the 0.9% agarose gel and compared with that of pK16. One of the twenty plasmids tested, pBN53 (plasmid G in FIG. 2), was selected for further restriction analysis because it contained the EcoRI fragments of pK16 corresponding to K. lactis DNA plus other K. lactis fragments. The 13 kb XhoI DNA fragment from pBN53, containing K. lactis DNA, was subcloned into the SalI site of pKR1B. The resulting plasmid, pKR1B-LAC4-1 (FIG. 2) was used to transform the K. lactis mutant strain MS425. Transformants were first selected for G418 resistance (75 μg of antibiotic/ml of agar medium) and then tested for growth on MinLac plates. Six G4:8 resistant colonies were also Lac+ suggesting that the Lac+ phenotype was conferred by the plasmid. These data show that pKR1BLAC4-1 carries a DNA sequence that can complement the lac4 mutation in MS425.

Plasmids B (FIG. 2) and C (FIG. 2) were constructed by linearizing pKR1B-LAC4-1 at its unique SstII site followed by limited Bal31 treatment and SalI linker insertion. The precise extent of deletion towards the LAC4 side was established by DNA sequencing (Bhairi: 1984), while the deletion towards the other side was estimated by determining the size of the DNA fragment obtained after digestion of the plasmids with both SalI and XbaI. Plasmid E (FIG. 2) was generated by XmaIII digestion of pKR1B-LAC4-1 followed by self ligation. Plasmid D (FIG. 2) was constructed by linearizing pKR1B-LAC4-1 with SstII followed by partial digestion with XbaI, blunt ending with DNA polymerase I and ligation. The ligation mixture was used to transform E. coli DG75 for ampicillin and kanamycin resistance. Plasmid DNA was analyzed from several transformants to screen for the desired deletion plasmid.

EXAMPLE 5

To construct the S. cerevisiae that grows on lactose, a strain of L1582 was transformed with pKR1B-LAC4-1 and cells were selected for resistance to G418. The procedures of Webster, T. D. and Dickson, R. C., (1983) Gene 26:243-252 were used to transform and select G418 resistant transformants of S. cerevisiae. Ten G418 resistant transformants were colony purified on YEPD/G418 (200 μg/ml) plates and 62 purified colonies chosen at random were spotted on MinLac, YEPD/G418 (200 μg/ml), and YEPD plates, in that order. All 62 colonies grew on the G418 and YEPD plates. Only 12 colonies (19%) grew on the MinLac plates. In another experiment, $10^2$ to $10^3$ G418 resistant transformed cells were spread on MinLac plates. Again, 19% of the G418 resistant colonies grew on lactose. As a control, L1582 was also transformed with the parent vector pKR1B. The G418 resistant transformants produced therefrom were selected and plated at concentrations in the range of $10^2$ to $10^6$ per MinLac plate. No Lac+ transformants were ever observed.

EXAMPLE 6

To rule out the possibility that Lac+ cells were being produced as a result of some peculiarity of strain L1582, strain YNN27 of S. cerevisiae was also transformed. YNN27 was transformed with pKR1B-LAC4-1 and the G418 resistant transformants were selected. Resistant colonies were pooled and $10^2$ to $10^6$ cells were plated on MinLac plates. Only one cell in 250 G418 resistant cells produced a Lac+ colony, a frequence on the order of 1/50 that of strain L1582. Lac+ colonies were also never observed when YNN27 was transformed with parent vector pKR1B.

EXAMPLE 7

As additional evidence that pKR1B-LAC4-1 was responsible for the observed Lac+ phenotype, the simultaneous loss of the Lac+ and G418 resistance characteristics was determined. The G418 resistance phenotype was used to measure the presence or absence of the plasmid. This determination was based on the observation that vectors having ARS replicons are unstable and are lost from cells, particularly when no selective pressure is present. Lac+ L1582 were grown in YEPD medium without G418 selection for 10 generations. The frequency of G418 resistant cells decreased from 20% initially to 3%, indicating loss of the plasmid, and all 100 G418 sensitive cells tested at the end of the growth period by replica plating were Lac−. These results indicate that the Lac+ phenotype was mediated by the plasmid.

EXAMPLE 8

By contrast, when Lac+ YNN27 were grown in YEPD medium for 10 to 20 generations. more than 99% of the cells retained the G418 resistance marker, but only 10 to 30% were still Lac+. The stability of the G418 resistance phenotype suggested that the vector was integrating into a host chromosome.

EXAMPLE 9

Direct physical proof that Lac+ *S. cerevisiae* carried the pKR1B-LAC4-1, and that the plasmid had integrated into a host chromosome was obtained by Southern hybridization analysis using $^{32}$P-pKR1B-LAC4-1 as a hybridization probe. The Southern hybridization data are shown in FIG. 1. Total DNA was extracted from yeast using the procedure described in *Methods in Enzymology* (1980) 65:408-410 and electrophoresed on 0.9% agarose gels. DNA was transferred to nitrocellulose and hybridized to $^{32}$P-pKR1B-LAC4-1.

EXAMPLE 10

The kinetics of lactose transport were measured to determine if Lac+ *S. cerevisiae* transported measurable quantities of lactose and to determine the time scale over which the apparent initial velocity of transport could be measured. Lactose transport was measured using the following procedure. Saturated cultures of cells were obtained by growth at 30° C. in medium A: 10 g yeast extract, 20 g peptone, 100 ml of 20% lactic acid (titrated to pH 4.5 with solid sodium hydroxide) and 100 ml of 20% glycerol per liter, or medium B: 3.4 g yeast nitrogen base (Difco, without amino acids or ammonium sulfate), 10 g ammonium sulfate, 3 g 20 mg adenine, 20 mg uracil, 20 mg leucine, 20 mg histidine, 20 mg tryptophan, 20 mg methionine and 20 mg lysine per liter. Strain MS425/pKR1B of *K. lactis* was grown on medium A containing 10 µg G418/ml, while *S. cerevisiae* strains L1582/pKR1B, and YNN27/pKR1B were grown on the same medium containing 200 µg Gt18/ml Strains L1582 or YNN27 transformed with either plasmid A, B, or C (autonomous or integrated) were grown on medium B.

This procedure is a modification of the procedure described by Serrano, R. (1977) European J. of Biochem. 80:97-102. To prepare cells for transport measurements, a saturated culture was diluted into fresh medium and grown from 0.1 to $3+^{1}A_{600}$/ml. Cells were harvested by filtration (45 mm dia, 0.45 µm Millipore type HA), washed four times with 10 ml of ice cold distilled water, and then resuspended in 100 mM tartaric acid (titrated to pH 4.2 with sodium hydroxide) at 60 to 100 $A_{600}$/ml. At this point cells could be stored at 4° C. for up to 24 hours without loss of transport activity.

To measure lactose transport, a sample of cells, 0.3 to 1.0 ml, was warmed to 23° C. for 2 min, lactose was added to the desired concentrations and at zero time 0.luCi of D-Glucose-[$^{14}$C]lactose (CFA 278; 58 mCi/mM; Amersham Corp., Lexington, Mass.) was added per 0.3 ml of cells. At the indicated times 100 µl samples were filtered on 25 mm diameter Nuclepore filters (0.4µm pore size; Nuclepore Corp., Pleasanton, Cal.). The filter was washed twice with 5 ml of ice cold distilled water, dried and counted in 4 ml of a toluene-based cocktail containing 250 ml of triton X-100 and 6.5 g p-terphenyl per liter using a liquid scintillation counter. The specific activity, cpm/pmole of lactose, of each reaction was determined by counting a 10 µl sample. Data are expressed as pmoles of intracellular lactose per $A_{600}$. Background transport was measured using cells that were heated for 3 min at 90° C. Typical background was 25 to 30 cpm.

EXAMPLE 11

The lactose transport in Lac+ *S. cerevisiae* was determined to be an energy-dependent process, as it is in *K. lactis*. To measure energy dependence, cells were pre-incubated with 1 mM 2,4-dinitrophenyl for 20 minutes at ambient temperature and then the uptake of 1 mM $^{14}$C-lactose was measured. Lactose transport was inhibited 91% both in the Lac+ strain of *S. cerevisiae*, L1582/pKR1B-LAC4-1, and in the *K. lactis* strain MS425/pKR1B.

EXAMPLE 12

The growth rate of Lac+ *S. cerevisiae* was determined by measuring the doubling time of cells. Strains were pre-grown to logarithmic phase in MinLac medium, then diluted to fresh medium, and the $A_{600}$ was measured from 0.2 to saturation.

The invention has been described herein with reference to certain preferred embodiments. However, as obvious variations thereon will become apparent to those skilled in the art, the invention is not to be considered as limited thereto.

What is claimed is:

1. A Lac+ Saccharomyces yeast strain having β-galactosidase activity, said strain having been transformed by insertion of a vector carrying a Lac 12 Kluyveromyces yeast gene which confers on the strain the ability to utilize lactose as its sole carbon source when cultured under appropriate lactose utilization conditions.

2. The yeast strain of claim 1, being a *Saccharomyces cerevisiae* strain.

3. The yeast strain of claim 1, wherein
   a beta-galactosidase gene encoding the β-galactosidase activity is carried by the vector.

4. The yeast strain of claim 3, wherein
   the β-galactosidase gene is LAC 4.

5. The yeast strain of claim 1, wherein the Lac 12 Kluyveromyces yeast gene is a *K. lactis* gene.

6. The yeast strain of claim 1, having the ATCC Accession No. 20757.

7. The yeast strain of claim 1, having the ATCC Accession No. 20758.

8. a vector capable of replication and gene expression in yeast carrying a DNA fragment comprising a Lac 12 Kluyveromyces permease yeast gene.

9. The vector of claim 3, wherein
   the Lac 12 Kluyveromyces gene is a Lac 12 *K. lactis* gene.

10. The vector of claim 7, further carrying
    a beta-galactosidase gene.

11. The vector of claim 10, wherein
    the beta-galactosidase gene is LAC4.

12. The vector of claim 8, having the ATCC Accession No. 40186.

13. A LAC+ Saccharomyces yeast strain having the ability to ferment lactose directly from whey without an intermediate hydrolysis step, said eyast strain carrying the vector of claim 8 and a β-galactosidase gene capable of expression by the yeast strain.

14. A Saccharomyces yeast strain transformed with a vector capable of replication and gene expression in yeast, said vector carrying a DNA fragment comprising a Lac 12 Kluyveromyces yeast lactose permease gene and a β-galactosidase gene.

15. A method of preparing the yeast strain of claim 1, comprising
    inserting into a Lac− Saccharomyces yeast strain a vector carrying a Lac 12 Kluyveromyces permease gene to confer the strain the ability of utilizing lactose as its sole carbon source when cultured under appropriate carbohydrate utilization conditions.

16. The method of claim 15, wherein
the Saccaromyces yeast strain is *Sacchaomyces cerevisiae*.

17. The method of claim 15, wherein
the inserted vector plasmid further carries a beta-galactosidase gene.

18. A method for converting lactose contained in whey into ethanol, which comprises
treating whey with a Lac+ Saccharomyces yeast strain having $\beta$-galactosidase activity, said strain having been transformed by insertion of a vector carrying a Lac 12 Kluyveromyces permease yeast gene which confers on the strain the ability to utilize lactose as its sole carbon source when cultured under appropriate lactose utilization conditions.

* * * * *